United States Patent
Wang et al.

(10) Patent No.: US 9,868,938 B2
(45) Date of Patent: Jan. 16, 2018

(54) METHODS FOR ACCELERATED AND ENHANCED CARDIAC DIFFERENTIATION OF IPS CELLS BY ELECTRICAL STIMULATION

(71) Applicant: University of Cincinnati, Cincinnati, OH (US)

(72) Inventors: Yi-Gang Wang, Cincinnati, OH (US); Ha Won Kim, Cincinnati, OH (US); Ruilian Ma, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 14/995,997

(22) Filed: Jan. 14, 2016

(65) Prior Publication Data

US 2016/0201035 A1  Jul. 14, 2016

Related U.S. Application Data

(60) Provisional application No. 62/103,224, filed on Jan. 14, 2015.

(51) Int. Cl.
| | |
|---|---|
| *C12N 5/02* | (2006.01) |
| *C12N 5/00* | (2006.01) |
| *C12N 13/00* | (2006.01) |
| *C12N 5/077* | (2010.01) |
| *A61K 35/34* | (2015.01) |
| *C12N 5/074* | (2010.01) |

(52) U.S. Cl.
CPC ............ *C12N 5/0657* (2013.01); *A61K 35/34* (2013.01); *C12N 5/0696* (2013.01); *C12N 2506/45* (2013.01); *C12N 2529/00* (2013.01)

(58) Field of Classification Search
CPC ................ C12N 5/0657; C12N 5/0696; C12N 2506/45; C12N 2529/00
USPC .......................... 435/173.1, 173.8, 325, 377
See application file for complete search history.

(56) References Cited

PUBLICATIONS

Narsinh et al., 2011, Molecular therapy, vol. 9, No. 4, p. 635-638.*
Bellin et al., 2012, Nature reviews/Molecular Cell Biology, vol. 13, p. 713-726.*
Burridge et al., 2011, PLoS ONE, vol. 6, No. 4, e18293, p. 1-16.*
Wang, Yigang, 2014, New Journal of Science, vol. 2014, Article ID 756240, pp. 1-22.*
Nan Cao et al, "Ascorbic Acid Enhances the Cardiac Differentiation of Induced Pluripotent Stem Cells Through Promoting the Proliferation of Cardiac Progenitor Cells"; Cell Research (2012) 22: 219-236.
Dai Y, et al, "Effect of electrical stimulation on the differentiation of induced puripotent stem cells into cardiomyocytes induced by vitamin c in vitro"; Apr. 2013; 29(4): 364-7, found at http://www.ncbi.nlm.nih.gov/pubmed/23643166.
Kim SW et al, "Cardiac stem cells with electrical stimulation improve ischaemic heart function through regulation of connective tissue growth factor and miR-378"; Cardiovasc Res. Nov. 1, 2013; 100 (2): 241-51.
Mauritz et al, Generation of functional murine cardiac myocytes from induced pluripotent stem cells; Circulation, 2008 118 (5): 507-517.
Bowers et al, The extracellular matrix: at the center of it all; J Mol Cell Cardiol, 2010, 48(3): 474-482.
Ruben et al, Electrical signals affect the cardiomyocyte transcriptome independently of contraction; Physiol Genomics 42A: 283-289, 2010.
Cameron et al, Environmental magnetic fields: influences on early embryogenesis; Journal of Cellular Biochemistry, 417-425; 1993.
Chen et al, Cardiac differentiation of embryonic stem cells with point-source electrical stimulation; Conference Proceedings, IEEE Engineering in Medicine and Biology Society, 2008, pp. 1729-1732.
Sauer et al, Effects of electrical fields on cardiomyocite differentiation of embryonic stem cells; Journal of Cellular Biochemistry, 75 (4): 710, 723; 1999.
Serena et al, Electrical stimulation of human embryonic stem cells: cardiac differentiation and the generation of reactive oxygen species; Experimental Cell Research, 315 (20), pp. 3611-3619; 2009.
Huang et al, Molecular Strategy to Reduce In Vivo Collagen Barrier Promotes Entry of NCX1 Positive Inducible Pluripotent Stem Cells (iPSCNCX1+) into Ischemic (or Injured) Myocardium. PLoS ONE 8(8): e70023. doi:10.1371/journal.pone.0070023.

* cited by examiner

*Primary Examiner* — Shin Lin Chen
(74) *Attorney, Agent, or Firm* — Dinsmore & Shohl LLP (57) ABSTRACT

Methods of generating cardiomyocytes from induced pluripotent stem cells (IPSCs) are provided. More specifically, the present disclosure relates to methods of generating cardiomyocytes from iPSCs using electrical stimulation. In some aspects, uses of such cells for therapeutics and in methods of treatment are provided.

9 Claims, 8 Drawing Sheets

METHODS FOR ACCELERATED AND ENHANCED CARDIAC DIFFERENTIATION OF IPS CELLS BY ELECTRICAL STIMULATION

CROSS-REFERENCE TO RELATED APPLICATION

This application depends from and claims priority to U.S. Provisional Application No. 62/103,224 filed Jan. 14, 2015, the entire contents of which are incorporated herein by reference.

FIELD

The present disclosure relates to methods of generating cardiomyocytes from induced pluripotent stem cells (IPSCs). More specifically, the present disclosure relates to methods of generating cardiomyocytes from iPSCs using electrical stimulation. In some aspects, uses of such cells for therapeutics and in methods of treatment are provided.

BACKGROUND

Stem cells are pluripotent cells with remarkable potential to develop into many different cell types in the body during early life and growth. Stem cells hold promise for regenerative medicine and cell therapy, especially in fields where more personalized medicine approaches are becoming increasingly predominant. For example, a wide variety of progenitor/stem cell therapies are recognized as a promising strategy to repair damaged tissue, such as an ischemic damaged heart. In many tissues, stem cells essentially function as an internal repair system for living animals, dividing essentially without limit to replenish other cells. There are two types of stem cells: embryonic stem cells and non-embryonic "somatic" or "adult" stem cells. Induced pluripotent stem cells (iPSCs) are adult cells that have been genetically reprogrammed to pluripotent stem cells.

Although embryonic stem cells are attractive sources for cardiac regeneration due to their high capacity for unlimited proliferation and multipotency, there are several critical issues that need to be overcome for clinical application, including ethical concern and immunological rejection after transplantation. More recently, iPSCs have emerged as a promising cell source to differentiate into functional cardiomyocytes, which can be utilized to regenerate cardiac tissues. The iPSCs possess similar potential as embryonic stem cells in regards to their pluripotency, morphology, proliferative ability, surface antigens, gene expression, and epigenetic status of pluripotent stem cell-specific genes. Additionally, because iPSCs can be easily generated from patients own cells and have the similar potential as embryonic stem cells, generation of iPSC-derived cardiomyocytes is regarded as a promising strategy for treatment of ischemic heart without ethical and immunological issues.

Although stem cells carry promise, there are still challenges for using stem cells, particularly iPCSs for regenerative medicine and cell therapy. Although iPSCs can differentiate into functional cardiomyocytes through embryoid body (EB) differentiation in the presence of specific differentiation signals, the differentiation and reprogramming strategies are not standardized and are most often based on the addition of key growth factors at critical stages of development, making protocols expensive, poorly reproducible, and limited in terms of scale-up. Furthermore, low efficiency and low degree of maturation of cardiomyocytes that are differentiated from iPSCs still limit iPCSs potential for cardiac regeneration application, and no solid method has been established for enhancing iPSCs to differentiate into cardiomyocytes efficiently. Additionally, current differentiation or reprogramming protocols are too slow, and with some protocols currently taking more than a month to develop cardiomyocytes.

There is thus a need in the art to provide novel methods for the accelerated generation of cardiomyocytes from iPSCs.

SUMMARY

It is understood that both the following summary and the detailed description are exemplary and explanatory and are intended to provide further explanation of the disclosure as claimed. Neither the summary nor the description that follows is intended to define or limit the scope of the disclosure to the particular features mentioned in the summary or description.

One object of the present disclosure is to provide methods for the accelerated generation of cardiomyocytes from iPSCs, without the need of key exogenous growth factors which can make protocols expensive, poorly reproducible, and limited in terms of scale-up. This object is achieved by the present disclosure that provides methods of generating cardiomyocytes from induced pluripotent stem cells (iPSCs).

In some aspects, a method for the accelerated and enhanced generation of autologous cardiac cells is provided. In some aspects, the method comprises: applying electrical stimulation to induced pluripotent stem cells for a time period to induce cardiomyocyte differentiation of the induced pluripotent stem cells to form cardiomyocytes without the use of exogenous growth factors, wherein the exogenous growth factors selected from the group consisting of bone morphogenetic proteins, wingless/INT proteins, fibroblastic growth factors, vascular endothelial growth factor, activin A and ascorbic acid/vitamin C.

In other aspects, a method of treating a patent suffering from cardiac tissue deficiency, damage, or loss is provided. In some aspects, the method comprises applying electrical stimulation to induced pluripotent stem cells for a time period to induce cardiomyocyte differentiation of the induced pluripotent stem cells to form cardiomyocytes without the use of exogenous growth factors, wherein the exogenous growth factors selected from the group consisting of bone morphogenetic proteins, wingless/INT proteins, fibroblastic growth factors, vascular endothelial growth factor, activin A and ascorbic acid/vitamin C, and delivering one or more of the formed cardiomyocytes into a cardiovascular system component of the patient.

In further aspects, a method for the accelerated and enhanced generation of autologous cardiac cells is provided. In some aspects, the method comprises: seeding induced pluripotent stem cells on a substrate; cultivating the seeded induced pluripotent stem cells without exogenous growth factors, wherein the exogenous growth factors are selected from the group consisting of bone morphogenetic proteins, wingless/INT proteins, fibroblastic growth factors, vascular endothelial growth factor, activin A and ascorbic acid/vitamin C; and applying electrical stimulation to the seeded induced pluripotent stem cells for a time period to induce cardiomyocyte differentiation of the induced pluripotent stem cells to form cardiomyocytes.

BRIEF DESCRIPTION OF THE DRAWINGS

FIG. 1A: The timing of attached EBs derived from hiPSCs started beating under different electric fields. FIG. 1B: The percentage of contracting EBs from hiPSCs after induction with electric fields for up to 30 days. FIG. 1C: The beating frequency of attached EBs derived from hiPSCs after induction with electric fields for up to 30 days. *p<0.05. NS, no significant difference. Data are mean±SEM (n=6 per group).

FIG. 2A: The expressions of cardiac progenitor genes and pluripotent genes in differentiated hiPSCs were analyzed by qPCR. FIG. 2B: The protein levels of these cardiogenic markers in differentiated hiPSCs were analyzed by western blotting. FIG. 2C: Cardiogenic marker Nkx2-5 in differentiated hiPSCs was identified by immunostaining (Green). Nuclei shown by DAPI. Scale bars=100 μm. FIG. 2D: The percentage of Nkx2-5 or cTnT positive cells in differentiated hiPSCs was analyzed by FACS. The representative univariate histograms and the quantitative data were showed. Date are mean±SEM (n=4 per group).*vs control group, p<0.05.

FIG. 3A: The sarcomere formation was identified by immunostaining of α-actinin or cTnT (Red) in the hiPSC-CMs. Nuclei shown by DAPI. Scale bars=100 μm. FIG. 3B: The percentage of α-actinin-positive hiPSC-CMs was identified by FACS. The representative univariate histograms and the quantitative data were showed. FIG. 3C: The cardiac genes related to contractions after differentiation of hiPSCs into CMs were analyzed by qPCR. FIG. 3D: The intracellular $Ca^{2+}$ levels of cultured hiPSC-CMs (Blue line=control, Red line=EleS) was identified by Fluo-4 dye and quantified by FACS.*vs control group, p<0.05.**vs control group, p<0.01. Date are mean±SEM (n=4 per group).

FIG. 4A: Heatmap of RNA expression data illustrating differentially expressed genes in hiPSC-CMs induced with or without EleS. Red indicates up-regulated genes, and green indicates down-regulated genes. FIG. 4B: Gene Set Enrichment Analysis shows the biological processes activated by EleS. FIG. 4C: Data analysis also shows the canonical pathways activated by EleS.

FIG. 5A: The expression of calcium-binding proteins in differentiated hiPSCs with or without EleS was analyzed by qPCR. FIG. 5B: the expression of cardiac genes in differentiated hiPSCs was analyzed by qPCR after incubated with multiple calcium signaling inhibitors, including verapamil (calcium ion influx inhibitor), W-7 (CAML antagonist), and TMB-8 (intracellular $Ca^{2+}$ antagonist). FIG. 5C: The expression of genes related to cardiac differentiation and maturation in hiPSCs was analyzed by western blotting after incubated with multiple calcium signaling inhibitors. FIG. 5D: The schematic of calcium signaling pathways participating in cardiac differentiation of hiPSCs under EleS.*vs control group, p<0.05. NS, no significant difference. Date are mean±SEM (n=4 per group).

FIG. 6A: Representative M-mode echocardiograms in various treatment groups at 1 or 4-week after cell implantation. Yellow lines indicate LVDd and LVDs. FIG. 6B: EF and EF are showed. FIG. 6C: Heart tissue sections of various groups were stained with Masson's Trichome. The percentage of infarct size is showed.*vs PBS, p<0.05. # vs hiPSC-CM$^{Ctrl}$, p<0.05.

FIG. 8A: The expression of PKC, phosphorylated or total ERK in differentiated hiPSCs with or without EleS was analyzed by western blotting. FIG. 8B: The expression of PKC, phosphorylated or total ERK in EleS-induced hiPSC-CMs treated with TMB (TMB-8, inhibitor of both intracellular $Ca^{2+}$ and PKC) or CC (chelerythrine chloride, activator of MAPK pathways) was analyzed by western blotting. FIG. 8C: The expression of cardiac genes in EleS-induced hiPSC-CMs treated with ERK inhibitor U1026 was analyzed by western blotting. FIG. 8D: The schematic of calcium signaling and PKC/ERK participating in cardiac differentiation of hiPSCs under EleS.

DETAILED DESCRIPTION

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions or processes are described as using specific materials or an order of individual steps, it is appreciated that materials or steps may be interchangeable such that the description of the invention may include multiple parts or steps arranged in many ways as is readily appreciated by one of skill in the art.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The present disclosure provides methods for the accelerated generation of cardiomyocytes from iPSCs using electrical stimulation, without the need for key exogenous growth factors which can make protocols expensive, poorly reproducible, and limited in terms of scale-up. The generated cardiomyocytes can be used in a variety of research, diagnostic, and therapeutic applications, including, but not limited to, transplantation of the cells into a subject in need thereof (e.g., for cardiovascular system tissue repair, to prevent or treat a cardiovascular disease or condition) or for organ synthesis.

As such, a method for the accelerated and enhanced generation of autologous cardiac cells includes applying electrical stimulation to iPSCs for a time period to induce cardiomyocyte differentiation of the iPSCs to form cardiomyocytes. In certain aspects, the iPSCs include embryoid bodies.

The term "electric stimulation" as used herein includes exposing the iPSCs to an electric field. In certain aspects, the electrical stimulation is a biomimetic electrical stimulation. The term "biomimetic electrical stimulation," as used herein, refers to an electrical stimulus that is applied to the iPSCs in vitro during cultivation and for the differentiation and formation of the cardiomyocytes. The electrical stimulation applied to the tissue-engineered construct is such that it resembles the electrical stimulation received by a specific native tissue in vivo. For example, the iPSCs may be cultivated in the presence of an electrical stimulation that mimics the electrical stimulation received by a cardiac muscle tissue in vivo.

The electrical stimulation may be generated by any suitable method, system, and apparatus as known in the art. For example, commercially available cardiac stimulators, which can produce electrical stimuli that mimic the electrical stimuli received by native cardiac tissues in vivo, may be used in the preparation of cardiac constructs. Other methods include using impulse generators in custom-made electric circuits. The electric filed applied to the iPSCs in vitro can include a direct current electric field, a pulsed electric filed, a capacitatively coupled electric field, a closed loop electrical stimulation device on a microelectrode array, an electromagnetic field or pulsed electromagnetic field, or combinations thereof. In certain aspects, the C-pace EP (available from Ion Optix) is used for the generation and application of the electrical stimulation to the iPSCs in vitro. The term "electric stimulation," as used herein, does not include an electric or electromagnetic field associated with ambient conditions, such as, for example, an electric field generated by casual exposure to radios, telephones, desktop computers or similar devices. Electric stimulation includes exposing iPSCs to an electric field in vitro.

In some aspects, the electrical stimulation is applied to the iPSCs at an electric field strength of from about 1V/1.8 cm to about 1.5 V/1.8 cm. In other aspects, the electrical stimulation is applied to the iPCSs at an electric field strength of about 1V/1.8 cm, about 1.1V/1.8 cm, about 1.2V/1.8 cm, about 1.3V/1.8 cm, about 1.4V/1.8 cm, about 1.5V/1.8 cm, including any value or range therebetween.

In some aspects, the electrical stimulation is applied to the iPSCs using a biphasic square pulse. In certain aspects, the biphasic square pulse is applied to the iPSCs over about a 5 second period. In other aspects, the biphasic square pulse can be applied to the iPSCs over about a 1 second period, about a 2 second period, about a 3 second period, about a 4 second period, about a 5 second period, about a 6 second period, about a 7 second period, about a 8 second period, about a 9 second period, about a 10 second period, including any value or range therebetween.

In some aspects, the electrical stimulation, including the application of a biphasic square pulse, is applied to the iPSCs at about a 5 Hertz frequency. In other aspects, the electrical stimulation, including the application of a biphasic square pulse, is applied to the iPSCs at about a 2 Hertz frequency, at about a 3 Hertz frequency, at about a 4 Hertz frequency, at about a 5 Hertz frequency, at about a 6 Hertz frequency, at about a 7 Hertz frequency, at about a 8 Hertz frequency, at about a 9 Hertz frequency, at about a 10 Hertz frequency, including any value or range therebetween. In various aspects, the electrical stimulation can be applied to the iPSCs for a period of 1 day to a period of 30 days, including any value or range in between.

Previous methods for differentiating cardiomyocytes from iPSCs include the addition and subtraction of key growth factors and other supplements at critical stages of development, making protocols expensive, poorly reproducible, and limited in terms of scale-up. However, it was unexpectedly found that applying electrical stimulation in the absence of these key growth factors and other supplements resulted in a more accelerated and efficient process of generating cardiomyocytes from iPSCs in vitro. In certain aspects, the instant methods result in the generation of cardiomyocytes (beating EBs) from iPSCs after two days of electrical stimulation. In other aspects, the instant methods result in the generation of cardiomyocytes (beating EBs) from iPSCs after one day of electrical stimulation. Thus, in some aspects, the method is accomplished without the use of exogenous growth factors. "Exogenous growth factors", as used herein, includes key growth factors and small molecules that are added to the iPCSs in vitro to aid in the differentiation process of the iPSCs into cardiomyocytes. Such excluded exogenous growth factors can include bone morphogenetic proteins (including but not limited to BMP-2, BMP-4, BMP-6, or BMP-7), wingless/INT proteins (including but not limited to wingless/INT agonists and antagonists such as IWP-2, IWR-1, IWP-3, and XAV939), fibroblastic growth factors (including but not limited to basic fibroblastic growth factor), vascular endothelial growth factor, activin A, ascorbic acid/vitamin C, and small molecules SB-431542 and SB203580. In certain aspect, the exogenous growth factors are selected from the group consisting of bone morphogenetic proteins, wingless/INT proteins, fibroblastic growth factors, vascular endothelial growth factor, activin A and ascorbic acid/vitamin C.

In addition to the instant methods resulting in the generation of cardiomyocytes (beating EBs) from iPSCs after only one or two days of electrical stimulation, the percentage of contracting cardiomyocytes, including cardiac progenitor cells (CPCs), and contraction rate were significantly higher in electrical stimulation-treated group than the non-electrical stimulation-treated group. Beating cardiomyocytes and CPCs were confirmed using genetically encoded calcium indicator, GCaMP5 driven by troponin T gene promoter, which consists of a $Ca^{2+}$-sensitive calmodulin domain fused to GFP. Furthermore, expression of cardiac differentiation markers such as α-sarcomeric activin, TNNI3, αMHC, GATA4 and NKX2.5 were significantly increased by electrical stimulation, as examined by immunocytochemical analysis and real time PCR, compared to non-electrical stimulation group. Thus, the instant methods for differentiating cardiomyocytes from iPSCs result in accelerated differentiation of iPSCs into cardiomyocytes. Accelerated differentiation of iPCSs includes enhanced production of differentiation markers of cardiomyocytes, such as, for example, cardiac differentiation markers such as α-sarcomeric actinin, TNNI3, αMHC, GATA4 and NKX2.5, wherein "enhanced production" includes increased and/or accelerated production of such markers, as compared to control iPSCs that are not subjected to an electric or electromagnetic field but are otherwise under the same conditions.

In some aspects, the method for the accelerated and enhanced generation of includes seeding induced pluripotent stem cells on a substrate. The substrate can comprise an extracellular matrix proteins or components, such as vitronectin, fibronectin, collagen type IV, collagen type I, laminin, thrombospondin, vibronectin, proteoglycans, hyaluronan, and nidogen In certain aspects, the extracellular matrix protein includes vitronectin, (optionally in the form of Vitronectin (VTN-N) available from Thermo Fischer Scientific or Vitronectin XF™ available from Stem Cell Technologies).

In certain aspects, the present disclosure provides methods of tissue-engineered constructs comprising the differentiated cardiomyocytes produced by the instantly disclosed methods of applying electrical stimulation to iPSCs. More specifically, the inventive methods comprise contacting an appropriate substrate with the iPSCs to form a cell-seeded construct, and cultivating the resulting cell-seeded construct in the presence of a biomimetic electrical stimulation or electrical stimulation, as previously described, to form differentiated cardiomyocytes in a tissue-engineered construct. The cultivation is carried out under conditions and for a time period that allow the formation of a three-dimensional cell structure having structural and functional characteristics of tissue.

The substrate used in such methods is biocompatible. The term "biocompatible", as used herein, describes material which upon implantation does not provoke an undesirable adverse response in the patient, other than the expected response to the trauma of implantation. When introduced into a patient, a biocompatible material is not toxic or harmful to that patient, and does not cause immunological rejection. Depending on the intended purpose of the construct, the substrate may be biodegradable or non-biodegradable. The substrate may comprise a naturally-occurring polymer, a synthetic polymer, or any combination of naturally-occurring and/or synthetic polymers. When the construct is intended to be implanted, the cardiomyocytes may be autologous.

In further aspects, the present disclosure provides methods of treatment and compositions utilizing the differentiated cardiomyocytes produced by the instantly disclosed methods of applying electrical stimulation to iPSCs. In some embodiments, uses of such cells for research, compound screening and analysis, and therapeutics, such as personalized and regenerative medicine are provided.

For example, in one aspect the present disclosure provides a method of treating a patent suffering from cardiac tissue deficiency, damage, or loss. In some aspects, the method comprises applying electrical stimulation to induced pluripotent stem cells for a time period to induce cardiomyocyte differentiation of the induced pluripotent stem cells to form cardiomyocytes without the use of exogenous growth factors, wherein the exogenous growth factors selected from the group consisting of bone morphogenetic proteins, wingless/INT proteins, fibroblastic growth factors, vascular endothelial growth factor, activin A and ascorbic acid/vitamin C, and delivering an effective amount of one or more of the formed cardiomyocytes into a cardiovascular system component of the patient. In certain aspects, the cardiovascular system component of the patient is the heart. Biomimetic electrical stimulation or electrical stimulation is applied to the iPSCs in vitro, as previously described, to form the differentiated cardiomyocytes. In certain aspects, the cardiomyocytes may be autologous.

The term "treating" is used herein to characterize a method that delays or prevents the onset of a medical condition, slows down or stops the progression, aggravation, or deterioration of the symptoms of the condition, or cures the condition. The treatment may be administered prior to the onset of the disease, for a prophylactic or preventive action. It may also be administered after initiation of the disease, for a therapeutic action.

The term "delivering" in reference to the differentiated cardiomyocytes produced by the instantly disclosed methods of applying electrical stimulation to iPSCs means providing the a composition comprising the cardiomyocytes to the patient in need of treatment or prophylaxis. In certain aspects, delivering an effective amount of one or more of the formed cardiomyocytes into a cardiovascular system component of the patient comprises injection or implantation. The teen "implantation" refers to the medical operation by which cells or bioartificial tissue construct is put into the body of the patient. In certain aspects, wherein delivering comprises transplantation, the cardiomyocytes are delivered as a tissue, or alternatively, as a tissue-engineered construct comprising the differentiated cardiomyocytes. Thus, in certain aspects the cardiomyocytes are implanted at the site of the tissue defect or disease.

The "patient" to a human or another mammal that suffers from tissue deficiency, damage, or loss to a cardiovascular system component, such as the heart, or that suffers from disease or condition of the cardiovascular system. Such tissue deficiency, damage, or loss or disease can include coronary heart disease, cardiomyopathy, endocarditis, congenital cardiovascular defects, congestive heart failure, cardiac arrhythmia in a patient and tissue damage after myocardial infarction.

Thus, provided are methods to treat coronary heart disease, cardiomyopathy, endocarditis, congenital cardiovascular defects, congestive heart failure, cardiac arrhythmia, and tissue damage after myocardial infarction. The method comprises applying electrical stimulation to induced pluripotent stem cells for a time period to induce cardiomyocyte differentiation of the induced pluripotent stem cells to form cardiomyocytes without the use of exogenous growth factors, wherein the exogenous growth factors selected from the group consisting of bone morphogenetic proteins, wingless/INT proteins, fibroblastic growth factors, vascular endothelial growth factor, activin A and ascorbic acid/vitamin C, and delivering an effective amount of one or more of the formed cardiomyocytes into a cardiovascular system component of the patient. In certain aspects, the cardiovascular system component of the patient is the heart. Biomimetic electrical stimulation or electrical stimulation is applied to the iPSCs in vitro, as previously described, to form the differentiated cardiomyocytes. In certain aspects, the cardiomyocytes may be autologous.

The term "effective amount" as used herein means that amount of an agent (e.g., cardiomyocytes) that elicits the biological or medicinal response in a cell, tissue, organ, system, animal, or human that is being sought by a researcher, veterinarian, medical doctor, or other clinician. In some aspects, the effective amount is a "therapeutically effective amount" for the alleviation of the symptoms of the disease or condition being treated. In some aspects, the effective amount is a "prophylactically effective amount" for prophylaxis of the symptoms of the disease or condition being prevented.

In various aspects, the cardiomyocytes are implanted in the culture medium in which they are differentiated. In other aspects, the cardiomyocytes are isolated from the culture medium, and implanted. In further aspects, a pharmaceutically acceptable scaffold, as are known in the art, for the cardiomyocytes is implanted in the patient at the site at which the cardiomyocytes are implanted. Any suitable scaffold material may be used, including porous or semi-porous, natural, synthetic or semi-synthetic materials. As referred to herein, a "scaffold" is a material that contains or supports the cardiomyocytes, preferably enabling their growth at the site of implantation. The scaffold material may be implanted either before, after, or concurrent with implantation of the cardiomyocytes.

The present disclosure also provides compositions comprising the differentiated cardiomyocytes produced by the instantly disclosed methods of applying electrical stimulation to iPSCs, and a pharmaceutically acceptable carrier. Preferably the carrier is a scaffold material as discussed above.

The foregoing description is illustrative of particular aspects of the invention, but is not meant to be a limitation upon the practice thereof. In order that various aspects may be more readily understood, reference is made to the following examples which are intended to illustrate various aspects, but do not limit the scope thereof.

EXAMPLES

Example 1: Materials and Methods

Unless specified otherwise, the following experimental techniques were used in the Examples.

Human iPSC Culture and EB Formation

The human episomal iPSC line was adapted to feeder-free culture conditions (Life Technologies). The iPSCs were maintained in Essential 8™ culture medium (life technologies) coated culture dishes in Vitronectin (0.005 mg/ml, Life Technologies) at 37° C. in a humid atmosphere of 5% $CO_2$, and expanded for 3 to 4 days. The iPSCs that grew out from these colonies were digested in 1 mg/mL dispase solution (Gibco) at 37° C. for 3 to 5 minutes and placed in ultralow attachment plates (Corning) in suspension culture for 7 days. Differentiation medium (EB20), consisting of 80% high glucose DMEM, 0.1 mmol/L nonessential amino acids, 1 mmol/L L-glutamine, 0.1 mmol/L β-mercaptoethanol, and 20% FBS that was pretested for cardiac differentiation (Gibco), was used to initiate cardiac differentiation.

Electrical Stimulation of Embryoid Bodies

After 7 days of pre-culture, EBs were seeded on Vitronectin-coated 35 mm dish in differentiation medium (consisting of 80% high glucose DMEM, 0.1 mmol/L nonessential amino acids, 1 mmol/L L-glutamine, 0.1 mmol/L β-mercaptoethanol, and 20% FBS) for 12 hr followed by electrical stimulation (EleS) using a culture cell pacer system (IonOptix). To assess whether effects were dependent on stimulation voltage, EBs were subjected to EleS at 1 V or 1.5 V/1.8 cm with a biphasic square pulse (5 ms) at 5 HZ frequency for 1 to 30 days. EBs without EleS were used as baseline controls. Then, EBs were harvested and used for various molecular and cellular studies.

RNA Extraction and Real-Time PCR

Total RNA was isolated from various treatment groups of the cells with the RNeasy Mini kit (Qiagen), and cDNA was prepared using the Omniscript-RT kit (Qiagen). Each PCR was performed with specific primers. Real-time PCR was used to determine the expression of cardiac differentiation genes using the QuantiTect SYBR green PCR kit (Qiagen) and BIO-RAD-iQ5 optical module. The mRNA level was standardized to endogenous control (Gapdh) and expressed as fold changes.

Western Blot

The cells from various treatment groups were lysed with ice-cold cell lysis buffer plus protease inhibitor, pH 7.4 (Sigma). The protein samples (20 μg) were mixed and resolved in 6×SDS/PAGE sample buffer and boiled for 10 min before loading on proper polyacrylamide gels (Precast Gels, ISC Bioexpress). The electrophoresed proteins were transferred to nitrocellulose membranes (Bio-Rad). The membranes were incubated for 60 min with 5% dry milk and Tris-buffered saline to block nonspecific binding sites.

Immunocytochemistry

The human iPSCs-derived cardiomyocytes were fixed with 4% paraformaldehyde for 15 min at 4° C., and permeabilized in 1% Triton X-100 in PBS followed by two washes with PBS. Samples were incubated with specific primary antibodies, and then, with their related secondary antibodies.

Flow Cytometry

Single-cell suspensions of differentiated iPSCs were trypsinized in a tube at 20 days after differentiation had begun. About $10^6$ cells were fixed on ice with 4% paraformaldehyde for 30 min and permeabilized in 0.1% saponin for 30 min follow with 1% FBS on ice 30 min. Thereafter, cells were stained with monoclonal anti-troponin-T antibody (NeoMarker, Fremont, Calif.), monoclonal anti-α-actinin (sarcomeric) antibody (Sigma) or Nkx 2.5 (Santa Cruz Biotechnology) followed by a secondary antibody, anti-mouse or anti-rabbit IgG-Cy5 for 1 hr at room temperature. Analysis was performed using a FACS Aria instrument (BD Biosciences). Cells with an adequate size and granularity were accounted for in the statistical analysis.

Experimental Model of Acute MI and Cell Transplantation

To minimize the immune rejection, 10 to 12 weeks old immune deficiency mice (Stock No: 001303) were purchased from The Jackson Laboratory. The ligation of left anterior descending coronary was performed as our previous publication[24]. Briefly, mice were anesthetized by intraperitoneal administration of 0.1% ketamine and 0.02% xylene. Heart was exposed by left-sided minimal thoracotomy and left anterior descending (LAD) coronary artery was ligated with 6-0 silk. The intramyocardial delivery of the hiPSC-derived CMs with or without EleS (n=4/group) was performed as described previously[25]. Four weeks later, the hearts were excised, quickly frozen in liquid nitrogen-cooled isopentane, sectioned in 6 μm-thick slices in a cryostat, and analyzed by immunocytochemistry staining.

Cardiac Function Assessment by Echocardiography

Transthoracic echocardiography (iE33 Ultrasound System; Phillips) was performed with a 15-MHz probe. Animals were placed supine on an electrical heating pad at 37° C. under light isoflurane anesthesia (usual maintenance level 1.5% isoflurane/98.5% oxygen). Hearts were imaged in 2-D long-axis view at the level of the greatest left ventricular (LV) diameter with animals under light general anesthesia. This view was used to position the M-mode cursor perpendicular to the LV anterior and posterior walls. LV end-diastolic and end-systolic diameters were measured from M-mode recordings. LV ejection fraction (EF) was calculated as: EF (%)=[left ventricular end-diastolic dimension (LVDd)$^3$ minus left ventricular end systolic dimension (LVDs)$^3$/(LVDd)$^3$]×100. LV minor axis fractional shortening (FS) was also determined as [(LVDd-LVDs)/LVDd]×100. All measurements were performed according to the American Society for Echocardiography leading-edge technique standards, and averaged over three consecutive cardiac cycles.

Statistical Analysis

All values were expressed as mean±SE. Comparison between 2 mean values was evaluated by an unpaired Student 2-tailed t-test, and between 3 or more groups was evaluated by one-way ANOVA followed by Bonferroni post-hoc analysis. Statistical significance was accepted at p<0.05.

Figure 1:
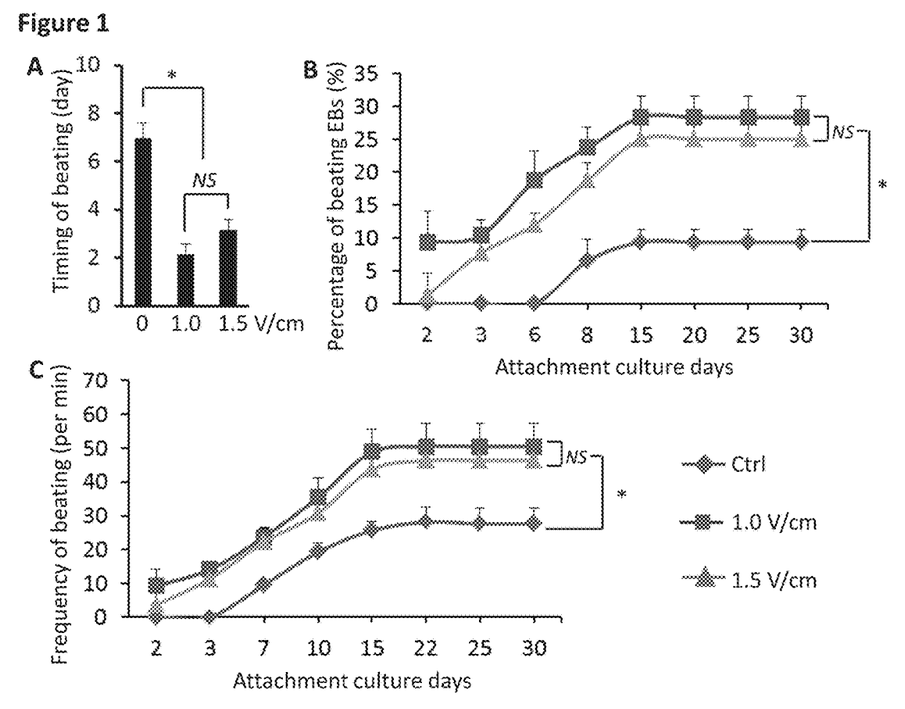
FIG. 1. Spontaneous cell beating of differentiated hiPSCs under electrical stimulation (EleS).

Example 2: EleS Enhances Spontaneous Cell Contracting/Beating of Differentiated hiPSCs Cardiomyocytes To determine the effect of EleS (1 or 1.5V/cm) on differentiated hiPSCs, the initial spontaneous contracting time was recorded daily. The attached EBs without EleS started contracting (cardiomyocytes) at 7.0±0.63 day (FIG. 1A). In contrast, the spontaneous beating of attached EBs (cardiomyocytes) with EleS can be observed as early at 2.1±0.40 day (1V/cm) or 3.2±0.40 day (1.5V/cm) (FIG. 1A). The percentage of beating EBs with EleS (1 or 1.5V/cm) was predominantly increased as compared to non-EleS treatment after attachment culture at each time point for up to 30 days (FIG. 1B). Furthermore, the contraction rate/frequency was increased from day 2 to day 30 in a time dependent manner, which was apparently higher under EleS as compared to non-EleS control (FIG. 1C). Although the contraction frequency of attached EBs under 1V/cm EleS was slightly higher than that under 1.5V/cm EleS, there was no statistically significant difference. We used 1V/cm EleS in the following experiments.

Figure 2:
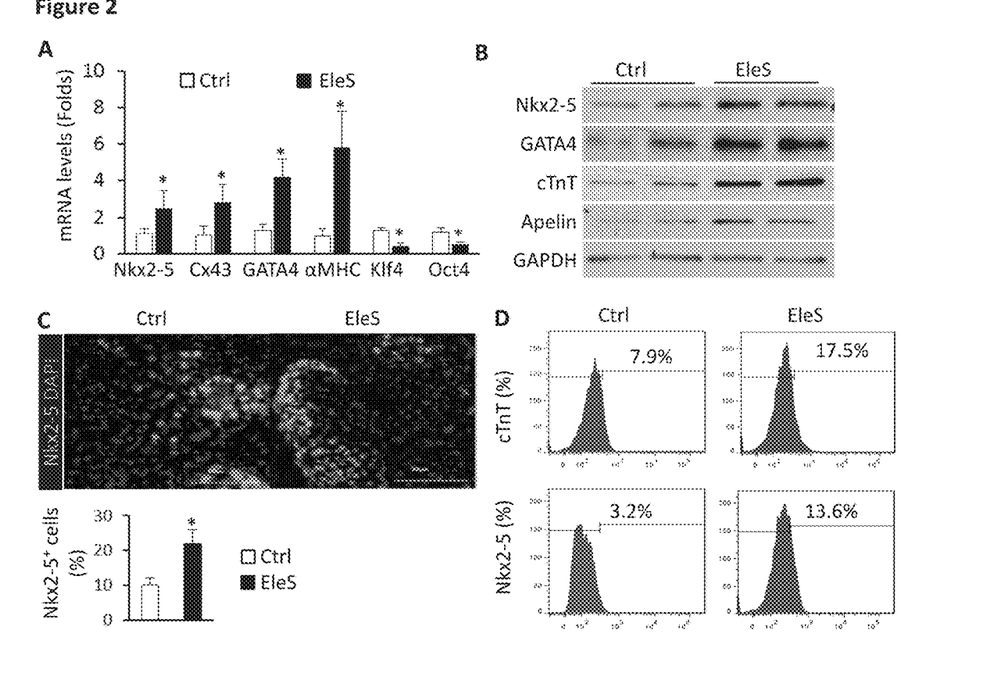
FIG. 2. EleS enhances the cardiomyogenic potential of hiPSCs.

Example 3: EleS Upregulates Cardiogenic Genes Expression of Differentiated hiPSCs It was assessed whether the cardiogenic genes were mediated by EleS during iPSCs differentiation. As compared to the non-EleS control group, the cardiac progenitor genes (Nkx2.5 and GATA4) and structural genes (αMHC and connexin43) were upregulated by EleS in hiPSCs after one-week induction, while the expression of pluripotent genes (Klf4 and Oct4) was decreased as examined by real-time PCR (FIG. 2A). The protein levels of these cardiogenic markers (such as Nkx2-5, GATA4, and cTnT) and peptides (such as Apelin[26]) were also significantly increased in differentiated hiPSCs under EleS conditioning as compared to the non-EleS control (FIG. 2B). The immunostaining also shows that the Nkx2-5 located in nuclei of differentiated hiPSCs was up-regulated by EleS conditioning (FIG. 2C). The CM differentiation efficiency of hiPSCs was enhanced by EleS as showed by FACS using antibodies against CM markers cTnT and Nkx2-5 (FIG. 2D).

Example 4: Eles Facilitates Functional Maturation of hiPSC-CMs

Figure 3:
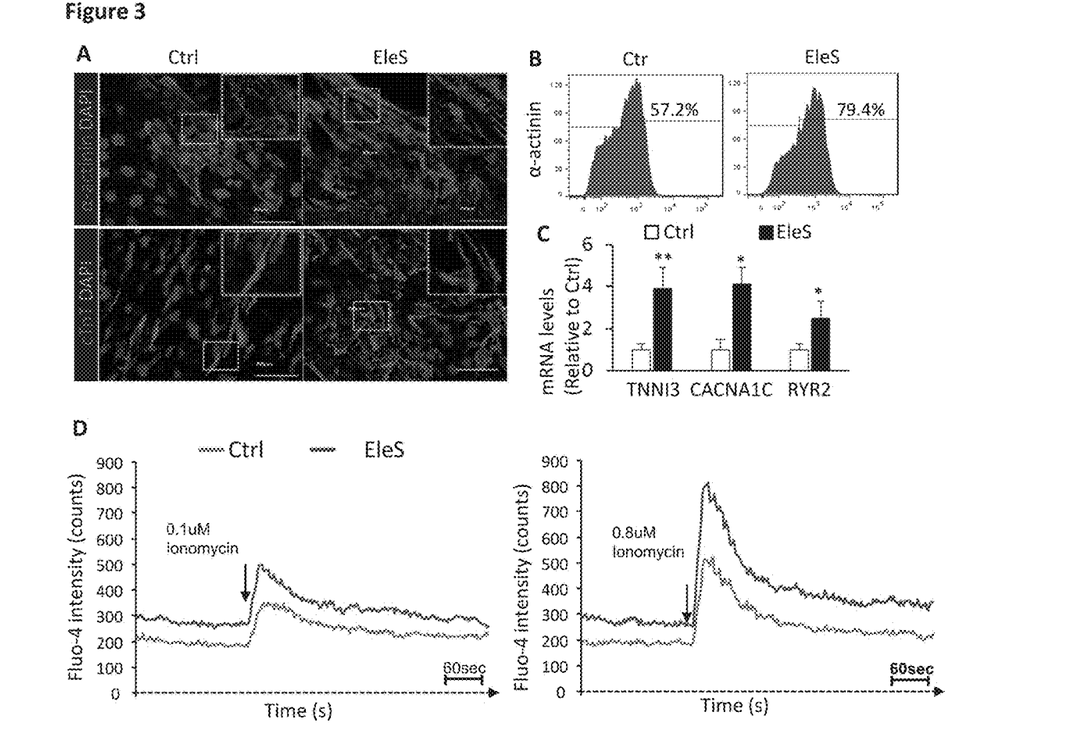
FIG. 3. EleS promotes functional maturation of hiPSC-derived CMs.

We further examined whether the hiPSC-CMs showed the functional features of mature cardiomyocytes. After EleS conditioning for two weeks, the immunostaining of α-actinin and cTnT shows that hiPSC-CMs displayed characteristic striations indicative of sarcomere formation, while the immature structure was observed in hiPSC-CMs without EleS (FIG. 3A). Almost 80% of hiPSC derivatives were α-actinin-positive CMs as identified by FACS (FIG. 3B). The cardiac genes (such as TNNI3, CACNA1C, and RYR2) related to functional maturation were up-regulated by EleS (FIG. 3C). Moreover, the spontaneous cellular $Ca^{2+}$ flux of hiPSC-CMs with EleS can be detected by the auto-fluorescence of cTnT-GCaMP calcium indicator using live cell imaging (data not shown). As shown by Fluo-4 dye, EleS treatment increased the intracellular $Ca^{2+}$ levels of cultured hiPSC-CMs as compared to control treatment (the baseline of FIG. 3D). In response to different dosages of ionomycin (a selective $Ca^{2+}$ ionophore), intracellular $Ca^{2+}$ levels of the hiPSC-CMs were significantly increased (FIG. 3D).

Example 5: The Global Gene Expression Profiles of hiPSCs During Differentiation

Figure 4:
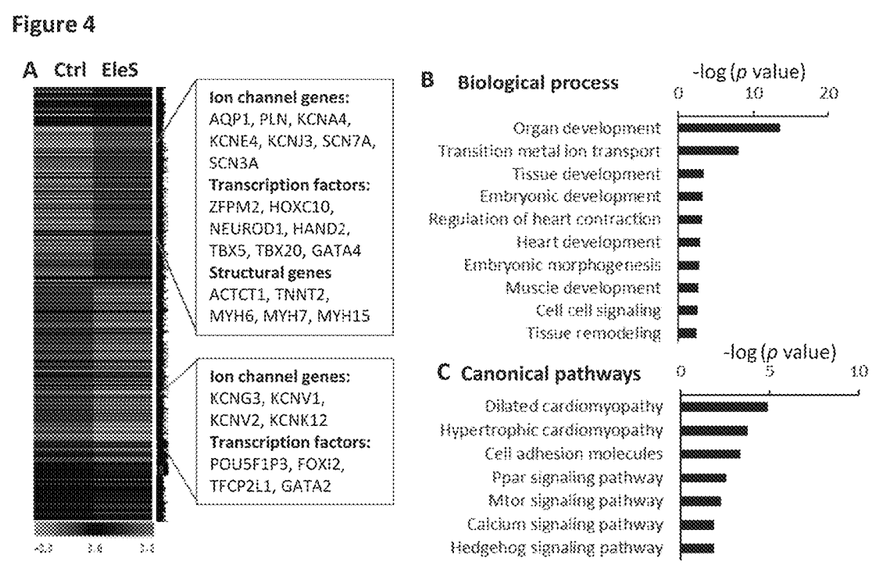
FIG. 4. Gene expression profiles of hiPSCs during CM differentiation.
Figure 7:
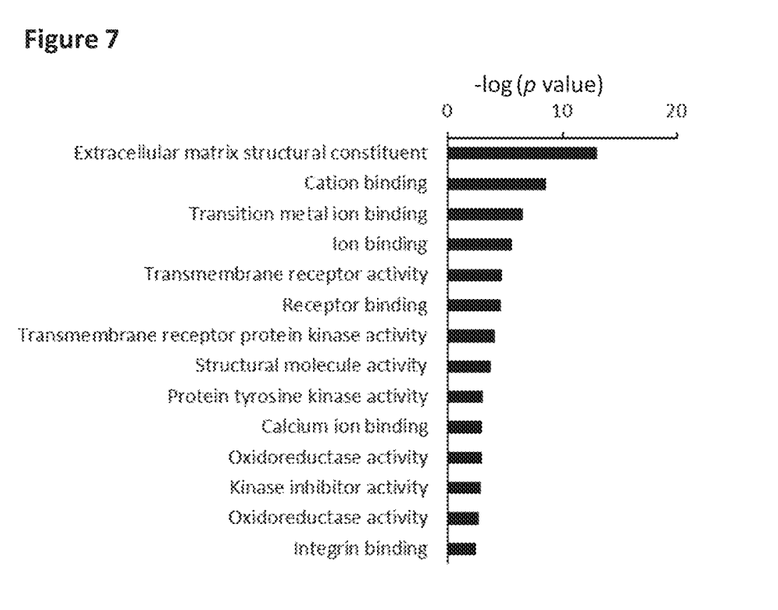
FIG. 7. The analysis of molecular function ontology in RNA-seq data between hiPSCs differentiated with or without EleS.

To identify the signal pathways activated by EleS, the global RNA profiles of hiPSCs were analyzed by RNA-sequencing after one-week induction with or without EleS. Selecting 2-fold change and p value<0.05 as cutoff threshold for data analysis, 558 genes were upregulated by EleS, while 513 genes were down-regulated (FIG. 4A). For instance, the cardiac transcription factors (such as HAND2 and TBX5) and construction genes (such as ACTCT1 and TNNT2) were up-regulated by EleS (FIG. 4A). The upregulated genes under EleS were investigated by Gene Set Enrichment Analysis in Molecular Signatures Database. Based on the biological process ontology, EleS enhanced the development processes including regulation of heart contraction and heart development (FIG. 4B). Moreover, the KEGG pathway analysis shows that the canonical pathways such as calcium signaling pathway were involved in EleS-induced differentiation of hiPSCs (FIG. 4C). According to molecular function ontology, several genes with ion binding activity were upregulated by EleS (FIG. 7), thus we further explored the specific signaling pathways related to electrophysiology.

Figure 5:
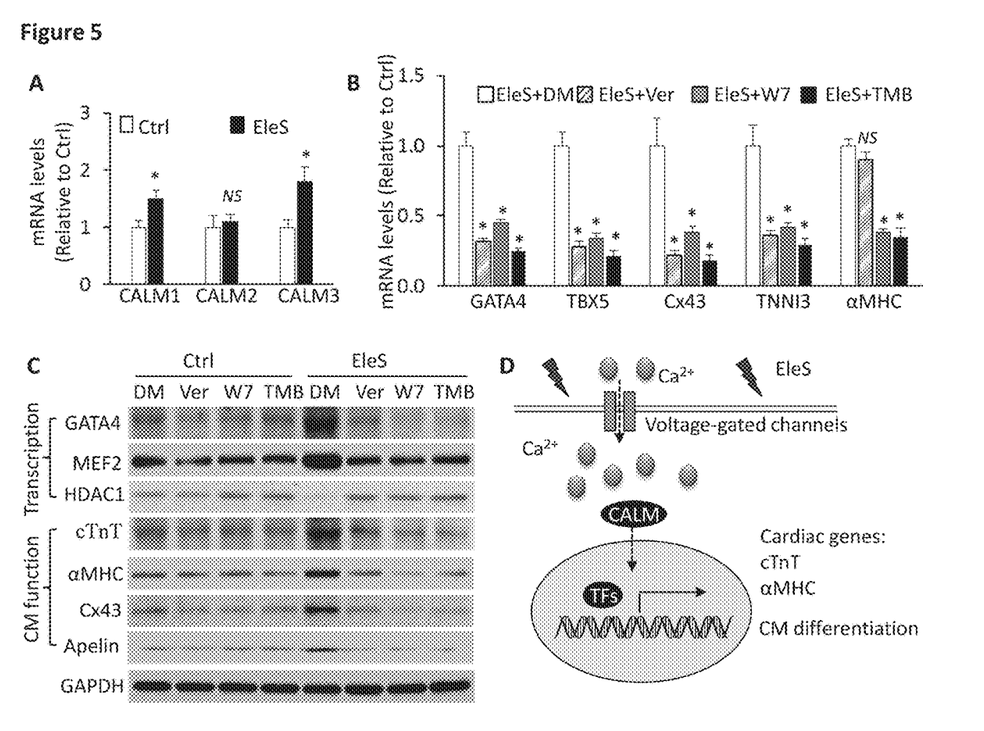
FIG. 5. EleS activates calcium signaling in hiPSCs.

Example 6: EleS Activates The Calcium Signaling Pathways During hiPSC Differentiation The $Ca^{2+}$ influx increased by electric or magnetic fields has been reported during cardiac differentiation[27-29], as consistent with our hiPSC models (FIG. 3D). However, it is still unclear how the cardiac commitment is influenced by the activated calcium signaling under EleS. $Ca^{2+}$-binding proteins (Calmodulin (CAML) 1 and 3) were up-regulated in hiPSCs by EleS induction for one-week (FIG. 5A). In hiPSCs induced with EleS, the expression of cardiac genes (GATA4, TBX5, Cx43, and TNNI3) was inhibited by multiple calcium signaling inhibitors, including verapamil ($Ca^{2+}$ ion influx inhibitor), W-7 (CAML antagonist), and TMB-8 (intracellular $Ca^{2+}$ antagonist), although αMHC was not significantly impacted by verapamil (FIG. 5B). Furthermore, Western blotting shows that the expression of cardiac transcription factors (GATA4 and MEF2) were enhanced by EleS in hiPSCs as compared to non-EleS control, but the effect of EleS was reversed by the calcium signaling inhibitors (FIG. 5C). Studies demonstrated that the down-regulation of histone deacetylase1 (HDAC1) can enhance chromatin acetylation in cardiac genes thereby promoting cardiac differentiation[30-32]. We also found that HDAC1 was down-regulated by EleS as compared to non-EleS control, but this effect was reversed by the calcium signaling inhibitors (FIG. 5C). The levels of the cardiac contraction proteins (cTnT and αMHC), gap junction proteins (Cx43), and cardiogenic peptides (Apelin) were also significantly increased in differentiated hiPSCs under EleS conditioning as compared to the non-EleS control, but the effect of EleS was abolished by the calcium signaling inhibitors (FIG. 5C). Thus, EleS enhances cardiac gene expression of hiPSCs through the activation of CAML genes in calcium signaling pathways (FIG. 5D).

Figure 8:
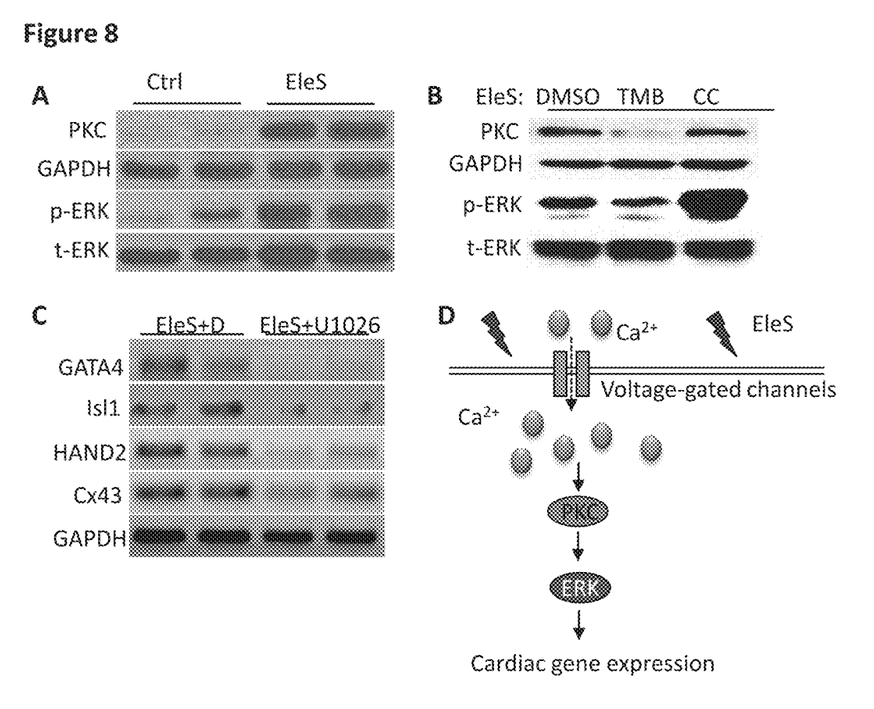
FIG. 8. Cross-talking of calcium signaling and ERK in hiPSCs under EleS.

Additionally, we found that PKC expression and ERK phosphorylation were enhanced by EleS in hiPSCs for one week (FIG. 8A). Under EleS, the treatment of TMB-8 (inhibitor of both intracellular $Ca^{2+}$ and $PKC^{33}$) can decrease the PKC expression and ERK phosphorylation as compared to DMSO treatment (FIG. 8B). The treatment of chelerythrine chloride (activator of MAPK pathways[34]) can increase ERK phosphorylation but not impact on the PKC expression compared to DMSO treatment (FIG. 8B). The expression of cardiac genes of hiPSCs under EleS was eliminated by ERK inhibitor U1026 (FIG. 8C). These data suggest that intracellular $Ca^{2+}$ and PKC is required for ERK phosphorylation and that activation of ERK cannot reversely impact on its upstream PKC expression (FIG. 8D).

Figure 6:
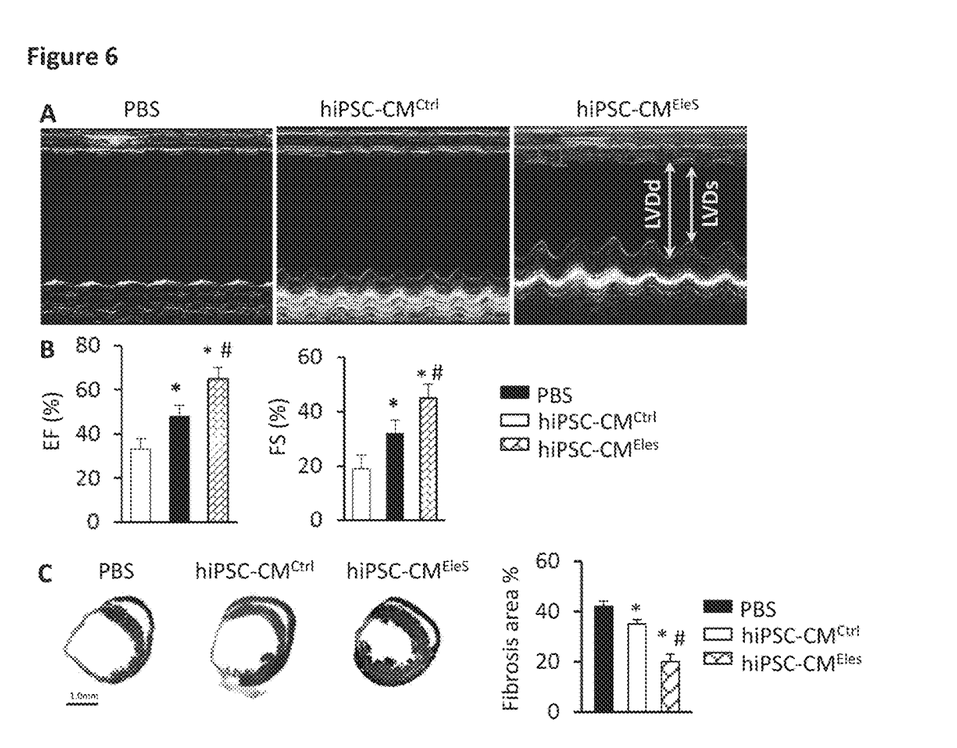
FIG. 6. The implanted hiPSC-CMs enhance the cardiac functional restoration of MI mice.

Example 7: EleS-Preconditioned hiPSC-CMs Improve Cardiac Functions of Ischemic Heart To evaluate the therapeutic effect of hiPSC-CMs, control-treated (hiPSC-CM$^{Ctrl}$) or EleS-preconditioned CMs (hiPSC-CM$^{EleS}$) were injected into infarcted heart of SCID mice. The cardiac function was assessed by echocardiograph after cell delivery. At 4-week after transplantation, the cardiac function of M1 mice was improved in hiPSC-CM$^{Ctrl}$ group, as demonstrated by decreasing LVDd and LVDs and increasing EF and FS as compared to the PBS treatment (FIG. 6A and FIG. 6B). The cardiac protective effect of hiPSC-CMs was significantly enhanced by EleS precondition as compared to the non-EleS treated cells (FIG. 6A and FIG. 6B). Concurrently, the microscopic analysis by Masson's trichrome staining showed that the average infarct area of hiPSC-CM$^{EleS}$ group was smaller than that of control groups (FIG. 6C). Thus, the cardioprotective effect of hiPSC-CM$^{EleS}$ was superior to that of the non-EleS treated cells.

Various modifications of the present invention, in addition to those shown and described herein, will be apparent to those skilled in the art of the above description. Such modifications are also intended to fall within the scope of the appended claims.

It is appreciated that all reagents are obtainable from commercial sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular aspects of the invention, but is not meant to be a limitation upon the practice thereof.

What is claimed:

1. An in vitro method for the accelerated and enhanced generation of cardiomyocytes, the method comprising: applying electrical stimulation to an embryoid body (EB) of human induced pluripotent stem cells (iPSCs) for a time period to induce cardiomyocyte differentiation of the induced pluripotent stem cells to form cardiomyocytes without the use of exogenous growth factors, wherein the exogenous growth factors are selected from the group consisting of bone morphogenetic proteins, wingless/INT proteins, fibroblastic growth factors, vascular endothelial growth factor, activin A and ascorbic acid/vitamin C, wherein generation of cardiomyocytes from human iPSCs is accelerated and enhanced when compared to in vitro generation from human iPSCs without applying electrical stimulation.

2. The method of claim 1, wherein the electrical stimulation is a biomimetic electrical stimulation.

3. The method of claim 1, wherein the electrical stimulation is applied to the induced pluripotent stem cells at an electric field strength of from about 1V/1.8 cm to about 1.5 V/1.8 cm.

4. The method of claim 3, wherein the electrical stimulation is applied to the induced pluripotent stem cells using a biphasic square pulse.

5. The method of claim 4, wherein the biphasic square pulse is applied to the induced pluripotent stem cells over about a 5 ms period.

6. The method of claim 5, wherein the electrical stimulation is applied at about a 5 Hertz frequency.

7. An in vitro method for the accelerated and enhanced generation of cardiomyocytes, the method comprising:
    seeding human induced pluripotent stem cells on a substrate;
    cultivating the seeded human induced pluripotent stem cells without exogenous growth factors, wherein the exogenous growth factors selected from the group consisting of bone morphogenetic proteins, wingless/INT proteins, fibroblastic growth factors, vascular endothelial growth factor, activin A and ascorbic acid/vitamin C; and
    applying electrical stimulation to an embryoid body (EB) of the seeded human induced pluripotent stem cells for a time period to induce cardiomyocyte differentiation of the induced pluripotent stem cells to form cardiomyocytes, wherein generation of cardiomyocytes from human induced pluripotent stem cells is accelerated and enhanced when compared to generation from human induced pluripotent stem cells without applying electrical stimulation.

8. The method of claim 7, wherein the electrical stimulation is a biomimetic electrical stimulation.

9. The method of claim 7, wherein the substrate comprises an extracellular matrix protein.

* * * * *